United States Patent [19]

Moore et al.

[11] Patent Number: 5,459,158

[45] Date of Patent: Oct. 17, 1995

[54] PHARMACEUTICAL COMPOSITIONS OF INDAZOLES AND METHODS OF USE THEREOF

[75] Inventors: Philip K. Moore, Thornton Heath; Rachel C. Babbedge, Northwood, both of Great Britain

[73] Assignee: Burroughs Wellcome Co., Research Triangle Park, N.C.

[21] Appl. No.: 168,246

[22] Filed: Dec. 17, 1993

[30] Foreign Application Priority Data

Dec. 18, 1992 [GB] United Kingdom .................. 9226377

[51] Int. Cl.$^6$ ................................................. A61K 31/415
[52] U.S. Cl. ...................................... 514/406; 548/360.1
[58] Field of Search ........................ 548/360.1; 514/406

[56] References Cited

U.S. PATENT DOCUMENTS

| | | | |
|---|---|---|---|
| 3,843,678 | 10/1974 | DiBella | 548/361.1 |
| 3,988,347 | 10/1976 | DiBella | 548/361.1 |
| 4,051,145 | 9/1977 | Dupre et al. | 548/360.1 |

FOREIGN PATENT DOCUMENTS

| | | |
|---|---|---|
| 518622 | 4/1953 | Belgium . |
| 2075346 | 6/1993 | Canada . |
| 0108890 | 5/1984 | European Pat. Off. . |
| 0372934 | 6/1990 | European Pat. Off. . |
| 0459819 | 12/1991 | European Pat. Off. . |
| 0459830 | 12/1991 | European Pat. Off. . |
| 5600 | 7/1966 | France . |
| 7631 | 1/1970 | France . |
| 2132527 | 11/1972 | France . |
| WO88/04293 | 6/1988 | WIPO . |

OTHER PUBLICATIONS

J. of Heterocyclic Chemistry vol. 22, No. 4 Jul.–Aug. 1985, pp. 985–991 Streef et al "Reactivity of some 3–substituted derivatives of 1,6–dihalogenopyridines . . . ".

Chemical Abstracts, vol. 91, No. 7, 1979 No. 56787h, "Rearrangements N–mono—and N,N–disubstituted . . . " Wladyslaw et al.

Biochemical Pharmacology vol. 31, No. 18, 1982, 1982, pp. 3002–3005 Murray "Inhibition . . . heterocycles".

Chemical Abstracts, vol. 102, No. 13, 1985 No. 113361m "Antiallergic activitiy . . . derivatives" Beyer.

Chemical Abstracts, vol. 118, No. 15, Apr. 1993 No. 139709m "7–Nitro indazole . . . blood pressure" Moore.

Chemical Abstracts, vol. 85, No. 7, 1976, 46664c; Floru, "Manufacture of 6–nitroindazole".

Primary Examiner—David B. Springer
Attorney, Agent, or Firm—Nixon & Vanderhye

[57] ABSTRACT

Indazoles of Formula (I)

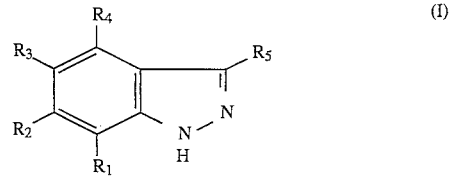

in which $R_1$, $R_2$, $R_3$ and $R_4$ are each separately selected from hydrogen, halogeno, halogenoalkyl, formyl, carboxy, sulpho, cyano, nitro, COR and $^+$NRR'R" groups, wherein R, R' and R" are each separately alkyl, aralkyl or aryl groups, and $R_5$ is selected from hydrogen, halogeno, halogenoalky, formyl, carboxy, sulpho, cyano, nitro, hydroxy, alkoxy, alkyl, COR, NHCOR and $^+$NRR'R" groups, wherein R, R' and R" are each separately alkyl, aralkyl or aryl groups, which may optionally be in the form of a physiologically acceptable ester or salt, are of value for use as an analgesic or in the treatment of any condition where the inhibition of brain/spinal cord nitric oxide synthase is advantageous, for example in neurodegenerative disease.

14 Claims, 2 Drawing Sheets

PHARMACEUTICAL COMPOSITIONS OF INDAZOLES AND METHODS OF USE THEREOF

BACKGROUND OF THE INVENTION

This invention relates to indazoles of value in therapy. U.S. Pat. No. 3,988,347 describes a process for the preparation of indazoles substituted at one or more of the 4-, 5-, 6- and 7-positions which are indicated to be useful as intermediates in the preparation of preservatives, dyestuffs and pharmaceuticals. U.S. Pat. No. 3,817,714 describes 1-substituted indazoles which are preparable from the compounds of U.S. Pat. No. 3,988,347 and which are useful for preserving aqueous compositions that are subject to decomposition and spoilage by the action of bacteria, for example latex paints. U.S. Pat. No. 3,817,714 further describes the possibility of using 1-unsubstituted indazoles as preservatives For aqueous compositions in the non-therapeutic contexts described in that patent.

The compound L-$N^G$-nitroarginine methyl ester has been described (Moore et al., British Journal of Pharmacology, 1991, 102,198–202) as blocking the enzyme nitric oxide synthase but is of little value as a therapeutic agent since it blocks this enzyme not only in the brain but also peripherally. We have now found that certain indazoles also block nitric oxide synthase and have the very particular advantage of being selective for the enzyme in the brain and elsewhere in the central nervous system.

DESCRIPTION OF THE INVENTION

Figure 1:
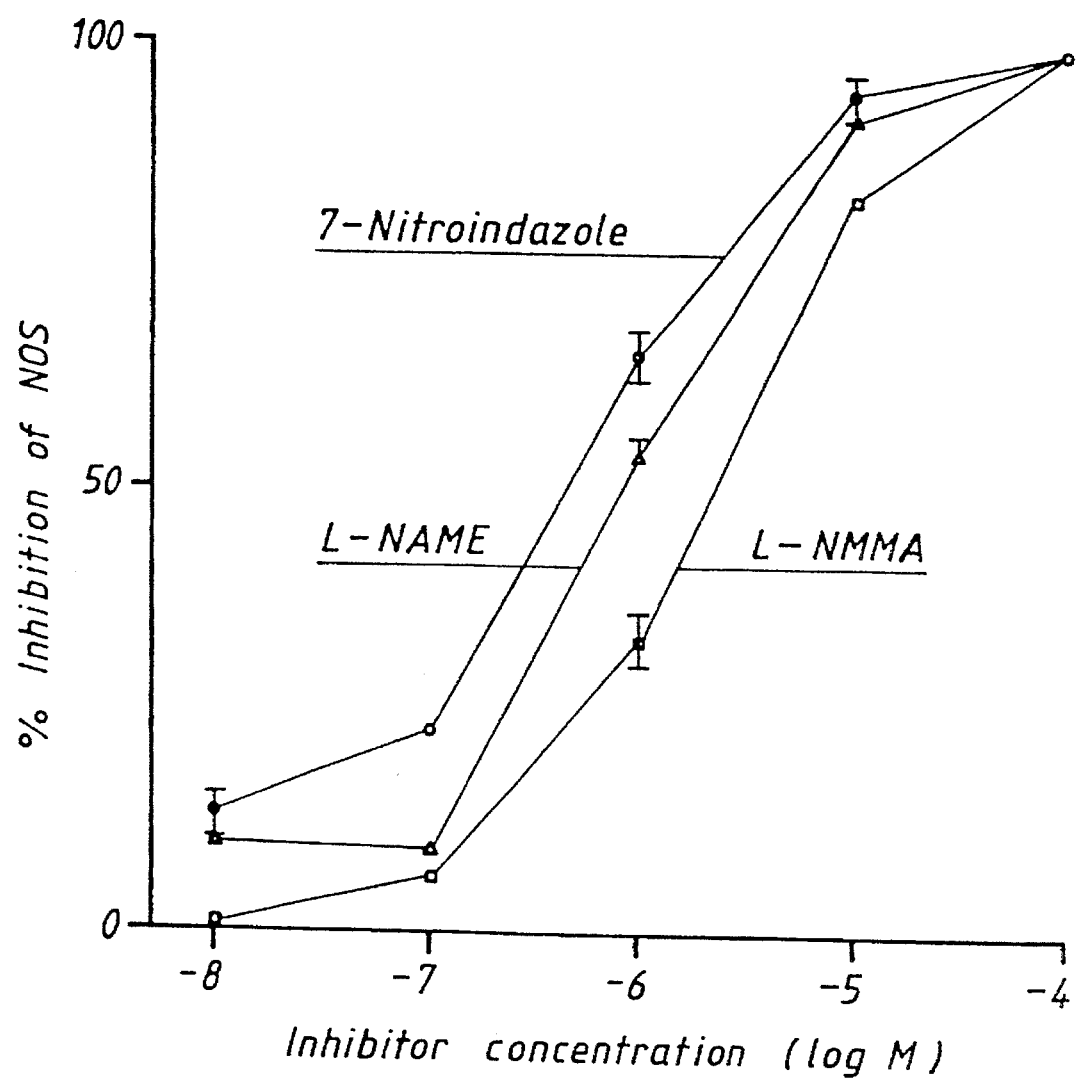
FIG. 1 is a graph showing the percent inhibition of nitric oxide synthase (NOS) for 7-nitroindazole, L-$N^G$-nitroarginine methyl ester (L-NAME) and L-$N^G$-monomethylarginine (L-NMMA) at various concentrations in Example 2.

Accordingly the present invention comprises a compound which is an indazole of formula (I)

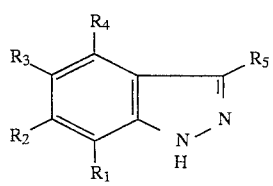

in which $R_1$, $R_2$, $R_3$ and $R_4$ are each separately selected from hydrogen, halogeno, halogenoalkyl, formyl, carboxy, sulpho, cyano, nitro, COR and $^+$NRR'R" groups, wherein R, R' and R" are each separately alkyl, aralkyl or aryl groups, and $R_5$ is selected from hydrogen, halogeno, halogenoalkyl, formyl, carboxy, sulpho, cyano, nitro, hydroxy, alkoxy, alkyl, COR, NHCOR and ⁻NRR'R" groups, wherein R, R' and R" are each separately alkyl, aralkyl or aryl groups, the compound optionally being in the form of a physiologically acceptable ester or salt, for use in therapy.

The standard system of numbering is used herein for the indazole ring system as shown below

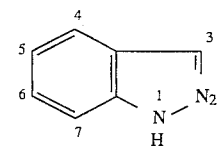

As regards the groups $R_1$, $R_2$, $R_3$ and $R_4$, the halogeno and halogenoalkyl groups may For example be a fluoro, bromo, iodo or particularly a chloro group or a $C_{1-12}$, particularly $C_{1-6}$, straight or branched chain alkyl group, for example an ethyl or especially a methyl group, substituted by one or more, for example three, such halogeno groups. Aralkyl and aryl groups R, R' and R" may conveniently be or contain various forms of aromatic hydrocarbyl group but 1- or 2-naphthyl and particularly phenyl groups are of most interest. Alkyl and aralkyl groups R, R' and R" may conveniently be or contain alkyl groups such as are described above in relation to the halogenoalkyl groups $R_1$, $R_2$, $R_3$ and $R_4$. Particular examples of groups COR and $^+$NRR'R" are thus propionyl and especially acetyl, and triethylamino and especially trimethylamino. As regards the group $R_5$, similar comments apply to halogeno, halogenoalkyl, COR and $^+$NRR'R" groups as for $R_1$ to $R_4$ whilst the alkyl groups $R_5$ may conveniently be selected similarly to the alkyl portion of the halogenoalkyl groups $R_1$ to $R_5$ and the groups R in NHCOR may conveniently be selected as for the groups R in COR and ⁻NRR'R", the group NHCOR being for example propionamido or acetamido.

Although each of the groups $R_1$ to $R_4$ may be hydrogen it is preferred that at least one is other than hydrogen, particularly the group $R_3$ or $R_2$ or especially $R_1$, although preferably two or three of $R_1$ to $R_4$ are hydrogen. As regards the groups which are other than hydrogen, the groups which are preferred are those which effect a significant degree of electron withdrawal from the benzene ring. Accordingly a nitro group is of particular interest. Other groups of interest, possibly together with another type of group such as nitro, are halogenoalkyl and especially halogeno groups.

Although groups $^+$NRR'R", for example trialkylamino groups such as trimethylamino, also possess this ability their charged nature is a disadvantage in terms of entry into the brain across the blood/brain barrier.

It will be appreciated that where more than one of $R_1$ to $R_4$ is other than hydrogen the two or more substituents may differ From each other. Conveniently however at least one, for example $R_1$, is one of the groups just indicated as being of interest.

Although $R_5$ may be other than hydrogen, for example a halogeno group such as chloro, it is preferably hydrogen.

As indicated, the indazoles (I) can be used in the form of physiologically acceptable salts. These may be Formed with various suitable inorganic and organic acids. Examples of such inorganic acids are phosphonic acid, nitric acid, sulphuric acid and particularly the hydrohalic acids hydrochloric acid, hydrobromic acid and hydroiodic acid. Examples of such organic acids are citric acid, oxalic acid, fumaric acid, maleic acid, lactic acid, succinic acid, malic acid, tartaric acid and methane sulphonic acid. Moreover, when one or more of $R_1$ to $R_5$ is a group $^+$NRR'R" the compound will be a quaternary ammonium salt which contains one or more physiologically acceptable artions. Such anions may for example correspond to those present in the acid addition salts just described but halogeno groups such as chloro and bromo are preferred.

Furthermore, when an acid substituent $R_1$ to $R_5$ such as carboxy or sulpho is present then the physiologically acceptable salt may be one Formed with a suitable base, examples of which are the alkali metal hydroxides, for example sodium hydroxide, quaternary ammonium hydroxides and amines such as tris (tris representing 2-amino-2-hydroxymethyl propane 1,3-diol).

When a carboxy or sulpho substituent is present or when a hydroxy group is present the indazoles (I) can be used in the Form of physiologically acceptable esters. Such esters may be Formed respectively with a suitable phenol or alcohol or with a suitable organic acid or even inorganic acid. Of particular interest are esters formed with a $C_{1-12}$, particularly $C_{1-6}$alkanol, For example ethyl and especially methyl esters.

Examples of specific indazoles (I) of use in the present invention are indazole and its 4-, 5-, 6- and 7-nitro derivatives together with their halogeno, for example chloro, analogues. Of these indazole and the last three mentioned nitro derivatives, especially 7-nitroindazole, are of particular interest.

The indazoles (I) can be prepared using various routes to indazoles described in the literature, for example the process of U.S. Pat. 3,988,347 which involves reaction of o-methylacetanilide containing the appropriate substituents $R_1$ to $R_4$ or substituents convertible thereto. Indazoles (I) having a substituent at the 3-position, i.e. containing a group $R_5$ other than hydrogen may be prepared by other procedures described in the art of indazole chemistry or by modifications of those procedures. It will be appreciated that many of the indazoles (I) are compounds known per se but, where this is not the case, the invention extends to such indazoles (I) per se which are novel.

The compounds may be prepared directly in salt form or converted thereto by reaction of the indazole with the appropriate acid or base. Esters may similarly be prepared directly or through reaction of the corresponding indazole containing a carboxy or sulpho group with the appropriate alcohol or of the corresponding indazole containing a hydroxy group with the appropriate acid.

The indazoles (I) may be formulated with a physiologically acceptable diluent or carrier for use as pharmaceuticals for veterinary, for example in a mammalian context, and particularly for human use by a variety of methods. For instance, they may be applied as a composition incorporating a liquid diluent or carrier, for example an aqueous or oily solution, suspension or emulsion, which may often be employed in injectable form for parenteral administration and therefore may conveniently be sterile and pyrogen free. Oral administration may also be used, and indeed is preferred where possible. Although compositions for this purpose may incorporate a liquid diluent or carrier, it is more usual to use a solid, for example a conventional solid carrier material such as starch, lactose, dextrin or magnesium stearate. Such solid compositions may conveniently be of a formed type, for example as tablets, capsules (including spansules), etc.

Other forms of administration than by injection or through the oral route may also be considered in both human and veterinary contexts, for example the use of suppositories or pessaries. Another form of pharmaceutical composition is one for buccal or nasal administration, for example lozenges, nose drops or an aerosol spray.

Thus, the invention further includes a pharmaceutical composition comprising a compound of formula (I) as defined hereinbefore together with a physiologically acceptable diluent or carrier.

By virtue of their selective inhibition of nitric oxide synthase the indazoles (I) are of value in any therapeutic context in which inhibition of brain/spinal cord NO synthase is advantageous. Thus they are suitable for use firstly as analgesics and secondly in the treatment of acute neurodegenerative diseases, for example in the treatment of convulsions or particularly for prophylactic use in the prevention of an ischaemic incident and possibly also in memory enhancement, and also in the treatment of chronic neurodegenerative diseases, for example Parkinson's disease.

Compositions may be Formulated in unit dosage form, i.e. in the form of discrete portions each comprising a unit dose, or a multiple or sub-multiple of a unit dose. Whilst the dosage of active compound given will depend on various factors, including the particular compound which is employed in the composition and the mode of administration and type of condition to be treated, it may be stated by way of guidance that a satisfactory dose will often lie in the range of from about 1 to about 100 mg/kg, particularly from about 10 to about 100 mg/kg, although doses outside this range may be used where appropriate.

The present invention thus also includes a method for the treatment of a patient benefiting from the inhibition of brain/spinal cord NO synthase, particularly a patient requiring analgesia or suffering from chronic or especially acute neurodegenerative disease, which comprises administering to such a patient in need thereof a therapeutically effective amount of a compound of formula (I) as defined hereinbefore. The invention is illustrated by the following Examples.

EXAMPLES

Example 1

Formulation of medicaments (A) Tablets of the following composition are prepared:

|  | mg/tablet |
| --- | --- |
| 7-nitroindazole (micronised) | 250 |
| 'Avicel' (microcrystalline cellulose) | 38 |
| polyvinylpyrrolidone | 3 |
| alginic acid | 6 |
| magnesium stearate | 3 |

The 7-nitroindazole is mixed with 'Avicel' and polyvinylpyrrolidone is added, dissolved in sufficient industrial methylated spirits (74° OP) to produce a mass suitable for granulating. The mass is granulated through a 20 mesh sieve and the resultant granules are dried at a temperature not exceeding 50° C. The dried granules are passed through a 20 mesh sieve and the alginic acid and magnesium stearate are then added and mixed with the granules. The produce is compressed into tablets each weighing 300 mg on ⅜ inch flat bevelled edge divided punches.

(B) Tablets of the following composition are prepared:

|  | mg/tablet |
| --- | --- |
| 7-nitroindazole (micronised) | 250 |
| 'Avicel' (microcrystalline cellulose) | 134 |
| polyvinylpyrrolidone | 4 |
| alginic acid | 8 |
| magnesium stearate | 4 |

The tablets are prepared by essentially the same procedure as described in (A) and are compressed at a tablet weight of 400 mg on 7/16 inch flat bevelled edge punches.

(C) Tablets of the following composition are prepared:

|  | mg/tablet |
| --- | --- |
| 7-nitroindazole (micronised) | 250 |
| lactose (300 mesh) | 19 |
| maize starch | 15 |
| gelatine | 10 |
| magnesium stearate | 6 |

The 7-nitroindazole is mixed with lactose and half the total quantity of maize starch required, and a 5% solution of gelatine in water is added to the mass. The product is granulated through a 16 mesh sieve, and the resultant granules are dried to constant weight at a temperature not exceeding 50° C. The dried granules are passed through a 20 mesh sieve and mixed with magnesium stearate and the remainder of the maize starch. The product is compressed at a 300 mg tablet weight on 3/8 inch flat bevelled edge divided punches.

Example 2

In vitro tests of 7-nitroindazole activity

Nitric oxide synthase (NOS) activity was determined in vitro by the method of Dwyer et al., Biochem. Biophys. Res. Commun. 1991, 176, 1136–1141. Mice (male, LACA, 28–32 g) were killed by cervical dislocation. Cerebella were removed, homogenized (1–10 w/v in 20 mM Tris buffer containing 2 mM EDTA, pH. 7.4) and aliquots (25 µl) incubated (37° C.) with L-arginine (120 nM) containing 0.5 µCi [$^3$H]-arginine (specific activity 62 Ci mmol$^{-1}$), NADPH (0.5 mM) and CaCl$_2$ (0.75 mM). Incubations also contained (a) 7-nitroindazole (MIM Research Chemicals Ltd.) in 0.5% w/v sodium carbonate solution (dissolution was effected by heating to 80° C. and cooling when the 7-nitroindazole remained in solution), (b) for comparative purposes, L-N$^G$-nitroarginine methyl ester (L-NAME) or L-N$^G$-monomethyl arginine (L-NMMA) in distilled water, or, (c) as control, an equal volume (5 µl) of 0.5% (w/v) sodium carbonate or distilled water. Final incubation volume was 105 µl. After 15 minutes the reaction was stopped by addition of 3 ml HEPES buffer (20 mM containing 2 mM EDTA, pH 5.5) and the [$^3$H]-citrulline produced was separated by cation exchange chromatography on 0.5 ml columns of Dowex AG50-W8 Na$^+$ form. [$^3$H]-Citrulline was quantitated by liquid scintillation spectroscopy of duplicate 1 ml aliquots of the flow-through.

In some experiments mice were injected i.p. with 7-nitroindazole (25 mg kg$^{-1}$) or L-NAME (50 mg kg$^{-1}$) and killed 15 minutes thereafter. Cerebella were removed, homogenized and NOS activity determined as described above.

It was found that 7-nitroindazole potently inhibited mouse cerebellar NOS in vitro (IC$_{50}$ 0.47±0.01 µM). For comparison, it was 1.8 times more potent than L-NAME (IC$_{50}$ 0.87±0.02 µM) and 5 times more potent than L-NMMA (IC$_{50}$ 2.37±0.03 µM), the detailed results being presented in FIG. 1. The results shown give the mean ± s.e. mean, n=6 (statistical analysis carried out by Student's unpaired t test). Where no error bar is indicated the error lies within the dimensions of the symbol. In separate experiments, administration of 7-nitroindazole (25 mg kg$^{-1}$, i.p.) decreased mouse cerebellar NOS activity measured 15 minutes thereafter by over 55% (3.9±0.06 nmol citrulline mg$^{-1}$ protein 15 min$^{-1}$, cf 9.1±0.26 arachis oil-injected controls, n=6, P<0.01). For comparison, a higher dose of L-NAME (50 mg kg$^{-1}$) produced only 46.2±1.6% inhibition of this enzyme under identical conditions (4.46±0.012 pmol citrulline mg$^{-1}$ protein 15 min$^{-1}$, cf 8.33±0.15 saline-injected controls n=6 P<0.01).

Example 3

In vivo tests of 7-nitroindazole activity

Anti-nociceptive activity of 7-nitroindazole (10–50 mg kg$^{-1}$) administered i.p. to mice as a suspension in arachis oil produced by sonication was determined by the formalin-induced hindpaw licking assay as described by Moore et al., British Journal of Pharmacology, 1991, 102, 198–202. Control animals received 10 ml kg$^{-1}$ of arachis oil or saline (0.9% w/v NaCl). This test shows hindpaw licking time (seconds) in the early (0–5 minutes) and late (15–30 minutes) phases on injection of 10 µl formalin (5% v/v) administered 15 minutes after the 7-nitroindazole.

In separate experiments, again described by Moore et al. (ibid), the blood pressure of urethane-anaesthetized (10 g kg$^{-1}$) mice was monitored for 45 minutes after i.p. administration of 7-nitroindazole.

Figure 2:
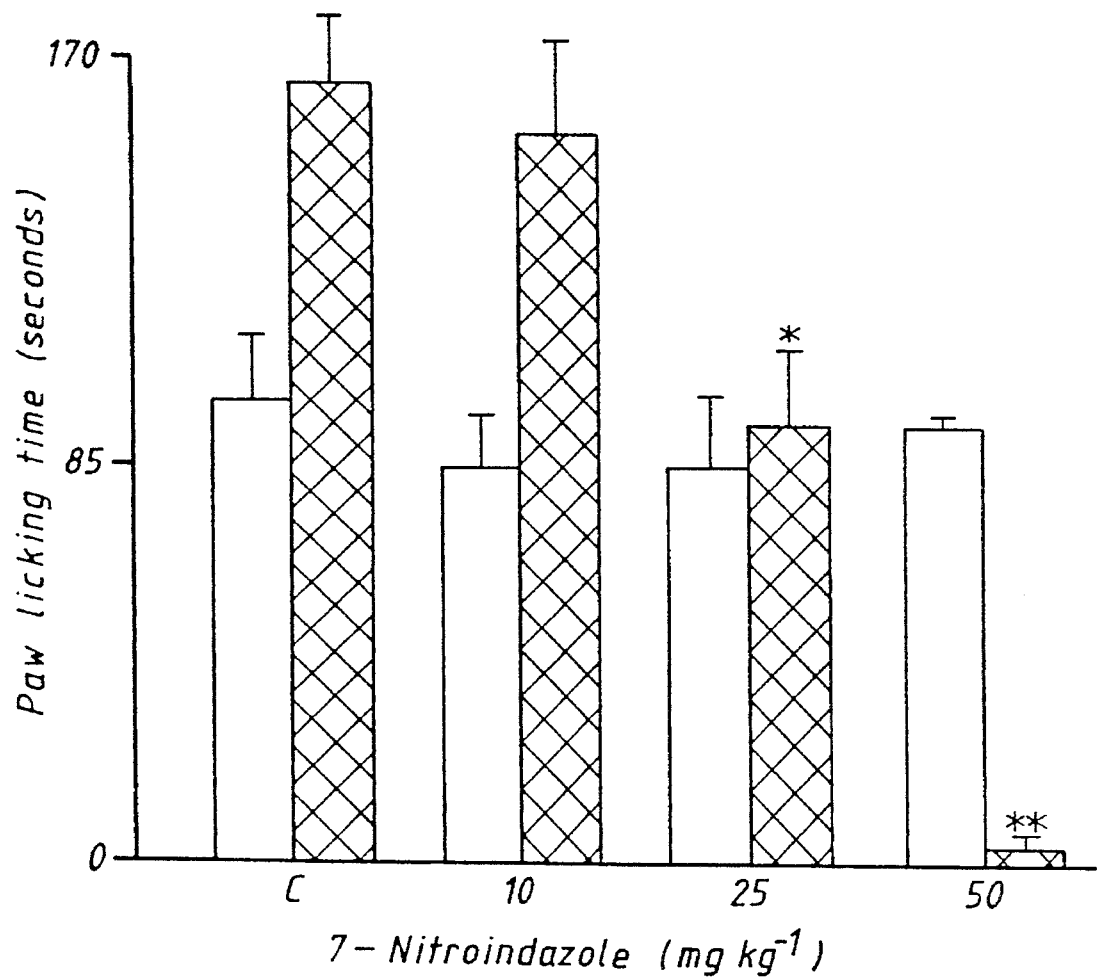
FIG. 2 is a bar graph comparing the paw licking time (early phase/late phase) achieved by three different concentrations of 7-nitroindazole as in Example 3.

7-Nitroindazole (10, 25 and 50 mg kg$^{-1}$) produced a dose-related inhibition of late phase formalin-induced hindpaw licking without influencing the early phase response. The detailed results are presented in FIG. 2 where open columns indicate the early phase (0–5 minutes) and hatched columns the late phase (15–30 minutes) hindpaw licking times. The mean ± s.e. mean is shown (statistical analysis by Student's unpaired t test), n=6–12, *P<0.03, **P<0.01. The control animals, identified by C, are those which received 10 ml kg$^{-1}$ arachis oil which, alone, did not influence hindpaw licking time. (The saline-injected mice gave an early phase value of 89.8±7.0 seconds and a late phase value of 150.7±11.5 seconds, n=15). The ED50 for the anti-nociceptive effect was 26 mg kg$^{-1}$ (equivalent to 159.5 µmol kg$^{-1}$).

Administration of 7-nitroindazole (25 and 80 mg kg$^{-1}$) did not increase mean arterial pressure. (MAP) over the 45 minute experimental period (e.g. 25 mg kg$^{-1}$, 47.4±5.1 mmHg cf 51.6±4.4 mmHG, n=4, before 7-nitroindazole administration, 80 mg kg$^{-1}$, 43.9±5.3 mmHg cf 49.5±2.9 mmHg n=4 before 7-nitroindazole administration). In control experiments, i.p. administration of arachis oil failed to alter MAP.

Example 4

In vitro and in vivo tests of other indazoles

The procedure of Example 2 was repeated for 7-nitroindazole and other indazoles but using rat cerebella. The IC$_{50}$ values so obtained for inhibition of rat cerebellar nitric oxide synthase (NOS) for various indazoles are shown in the Table below.

The procedure of Example 3 was repeated for 7-nitroindazole and other indazoles. The percentage inhibition of formalin-induced licking in the late phase following the administration of 50 mg kg$^{-1}$ i.p. of the indazoles is shown in the Table below. For the compound 5-nitroindazole, where an asterisk is shown, a pronounced sedative effect was produced which interfered with the determination of the anti-nociceptive effect so that it could not be quantitated. The other indazoles did not exhibit an overly sedative effect.

TABLE

| Compound | IC$_{50}$ NOS μM | Inhibition of licking (%) |
|---|---|---|
| indazole | 232 | 83.2 ± 12.2 |
| 5-nitroindazole | 56 | * |
| 6-nitroindazole | 32 | 67.0 ± 12.0 |
| 7-nitroindazole | 1 | 100 |
| 3-chloroindazole | 100 | not tested |
| 3-chloro-5-nitroindazole | 177 | not tested |

We claim:

1. A method of treating a condition in which inhibition of brain/spinal cord nitric oxide synthase is advantageous comprising administering to a mammal in need thereof an effective amount of a compound of formula (I)

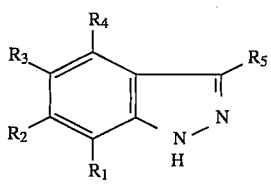

wherein $R_1$ to $R_4$ are selected from hydrogen or nitro and $R_5$ is hydrogen, $C_{1-4}$ alkyl or halo.

2. The method according to claim 1 wherein $R_1$ is nitro.

3. The method according to claim 1 wherein two or three of $R_1$ to $R_4$ are hydrogen.

4. The method according to claim 1 wherein the compound is 4-, 5- or 6-nitroindazole or a pharmaceutically acceptable salt thereof.

5. The method according to claim 1 wherein the compound is 7-nitroindazole or a pharmaceutically acceptable salt thereof.

6. The method according to claim 1 wherein the compound is indazole or a pharmaceutically acceptable salt thereof.

7. A pharmaceutical composition comprising a compound of formula (I)

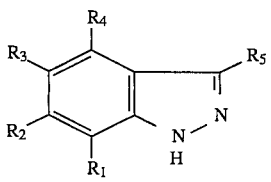

wherein $R_1$ to $R_4$ are selected from hydrogen or nitro and $R_5$ is hydrogen, $C_{1-4}$ alkyl or halo together with at least one pharmaceutically acceptable carrier.

8. The pharmaceutical composition according to claim 7 wherein the compound of formula (I) is 7-nitroindazole.

9. The pharmaceutical composition according to claim 7 wherein the compound of formula (I) is administered at a dosage of from 1 to 100 mg/kg.

10. The pharmaceutical composition according to claim 8 wherein the compound of formula (I) is administered at a dosage of from 1 to 100 mg/kg.

11. A method of causing analgesia comprising administering to a mammal in need thereof an effective amount of a compound of formula (I)

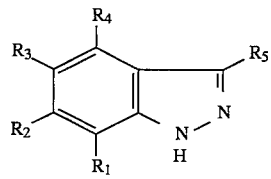

wherein $R_1$ to $R_4$ are selected from hydrogen or nitro and $R_5$ is hydrogen, $C_{1-4}$ alkyl or halo.

12. A method of treatment of an acute or chronic neurodegenerative disease comprising administering to a mammal in need thereof an effective amount of a compound of formula (I)

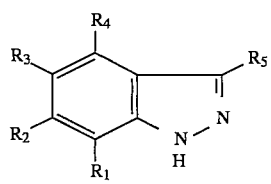

wherein $R_1$ to $R_4$ are selected from hydrogen or nitro and $R_5$ is hydrogen, $C_{1-4}$ alkyl or halo.

13. A method of treatment of convulsions comprising administering to a mammal in need thereof an effective amount of a compound of formula (I)

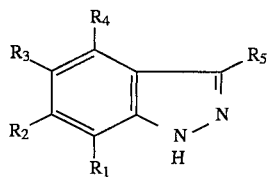

wherein $R_1$ to $R_4$ are selected from hydrogen or nitro and $R_5$ is hydrogen, $C_{1-4}$ alkyl or halo.

14. A method of treatment of Parkinson's disease comprising administering to a mammal in need thereof an effective amount of a compound of formula (I)

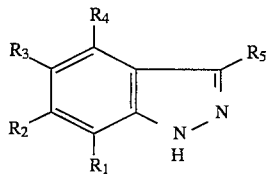

wherein $R_1$ to $R_4$ are selected from hydrogen or nitro and $R_5$ is hydrogen, $C_{1-4}$ alkyl or halo.

* * * * *